(12) United States Patent
Bunke et al.

(10) Patent No.: US 7,648,039 B2
(45) Date of Patent: Jan. 19, 2010

(54) PRESSURE-RESISTANT TANK FOR LIQUIDS

(75) Inventors: Claus Bunke, Sereetz (DE); Matthias Witt, Bad Schwartau (DE); Rainer Kunz, Lübeck (DE); Sven Heyer, Lübeck (DE); Thomas Rossen, Lübeck (DE); Henryk Schnaars, Lübeck (DE)

(73) Assignee: Dräger Medical AG & Co. KG, Lübeck (DE)

( * ) Notice: Subject to any disclaimer, the term of this patent is extended or adjusted under 35 U.S.C. 154(b) by 590 days.

(21) Appl. No.: 11/145,863

(22) Filed: Jun. 6, 2005

(65) Prior Publication Data

US 2006/0070622 A1    Apr. 6, 2006

(30) Foreign Application Priority Data

Aug. 27, 2004   (DE) .................. 10 2004 041 448

(51) Int. Cl.
  *B65D 6/00*  (2006.01)
  *B65D 6/32*  (2006.01)
(52) U.S. Cl. ....................... 220/4.12; 220/678
(58) Field of Classification Search ............... 220/4.12, 220/678, 677, 581, 586, 62.17, 62.11, 612, 220/611, 610; 219/121.14, 121.13; 128/203.27, 128/203.26, 203.17, 203.12; 215/12.1; 428/846.7, 428/328; 29/469, 462, 592
See application file for complete search history.

(56) References Cited

U.S. PATENT DOCUMENTS

| 2,720,203 | A | * | 10/1955 | Burns et al. | 128/203.12 |
| 2,785,679 | A | * | 3/1957 | Wullschleger | 128/200.18 |
| 3,162,192 | A | * | 12/1964 | Gardner et al. | 128/203.14 |
| 3,417,223 | A | * | 12/1968 | Steigerwald | 219/121.35 |
| 3,518,400 | A | * | 6/1970 | Gallivan | 219/121.14 |
| 3,597,339 | A | * | 8/1971 | Newman et al. | 205/107 |
| 3,771,214 | A | * | 11/1973 | Binger et al. | 228/262.5 |
| 4,108,688 | A | * | 8/1978 | Broverman | 148/549 |
| 4,160,149 | A | * | 7/1979 | Scheffels et al. | 219/121.14 |
| 4,194,043 | A | * | 3/1980 | Lee et al. | 428/582 |
| 4,386,261 | A | * | 5/1983 | Berglund et al. | 392/492 |
| 4,825,860 | A | | 5/1989 | Falb et al. | |
| 4,847,048 | A | * | 7/1989 | Nishi et al. | 420/547 |

(Continued)

FOREIGN PATENT DOCUMENTS

DE    35 23 948 C2    1/1987

(Continued)

OTHER PUBLICATIONS

Yun et al.. "Effects of Hudrogen in Lanthanum on Hydrogen Content in Al-alloy". Material Science and Engineering. Sep. 25, 2003, vol. 357, Issues 1-2, p. 409.*

*Primary Examiner*—Anthony Stashick
*Assistant Examiner*—Robert J Hicks
(74) *Attorney, Agent, or Firm*—McGlew and Tuttle, P.C.

(57) ABSTRACT

A pressure-resistant tank for liquids includes a plurality of differently shaped diecast parts (1, 2) made of a first aluminum alloy (cast alloy). The diecast parts (1, 2) are connected by means of a closed weld seam welded with an electron beam with the use of a second aluminum alloy (wrought alloy). The second aluminum alloy has especially a hydrogen content of less than 0.2 mL per 100 g of wrought alloy. The tank for liquids is especially an anesthetic tank and the anesthetic is desflurane.

20 Claims, 2 Drawing Sheets

U.S. PATENT DOCUMENTS

| | | | | |
|---|---|---|---|---|
| 4,854,343 | A | * | 8/1989 | Rilett .................... 137/543.19 |
| 5,505,236 | A | * | 4/1996 | Grabenkort et al. ......... 141/329 |
| 5,605,146 | A | * | 2/1997 | Sarela .................. 128/203.12 |
| 5,807,430 | A | * | 9/1998 | Zheng et al. ........... 106/287.11 |
| 5,966,951 | A | * | 10/1999 | Hallin et al. .................. 62/141 |
| 6,234,581 | B1 | * | 5/2001 | Stach .................... 301/64.102 |
| 6,394,087 | B1 | * | 5/2002 | Kankkunen et al. .... 128/203.16 |
| 6,672,306 | B2 | * | 1/2004 | Loser et al. ............ 128/203.12 |
| 2001/0004902 | A1 | * | 6/2001 | Garceau ..................... 137/264 |
| 2006/0042626 | A1 | * | 3/2006 | Bunke et al. ........... 128/203.22 |

FOREIGN PATENT DOCUMENTS

| | | | |
|---|---|---|---|
| FR | 2 263 061 | | 10/1975 |
| JP | 57115988 | A * | 7/1982 |
| JP | 58 154490 | | 9/1983 |
| JP | 10 227301 | | 8/1998 |

* cited by examiner

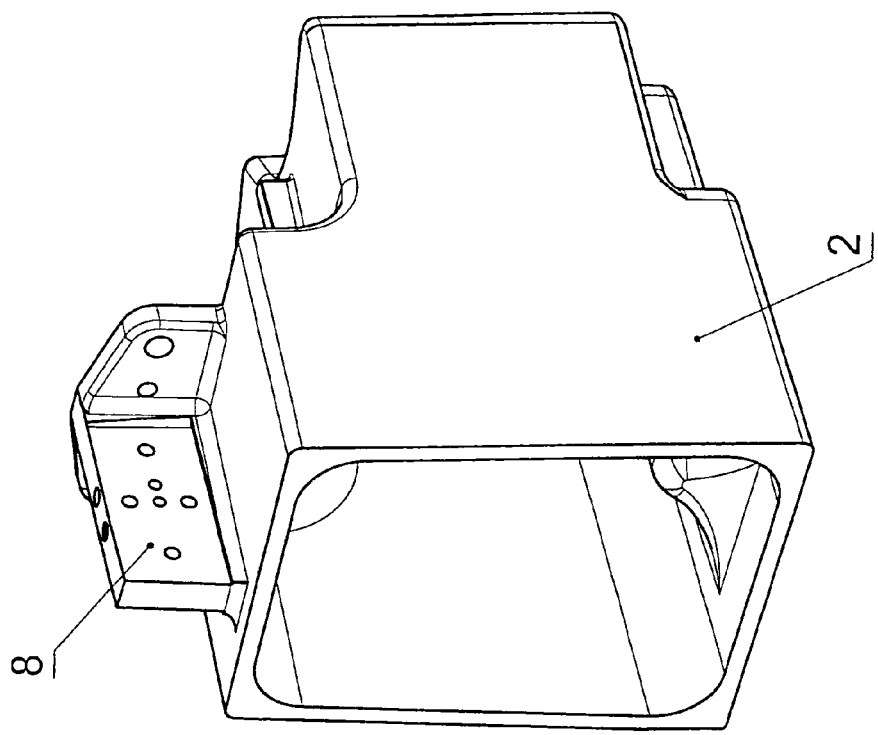
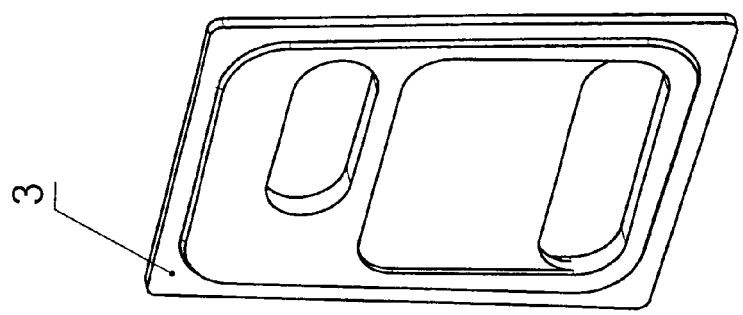
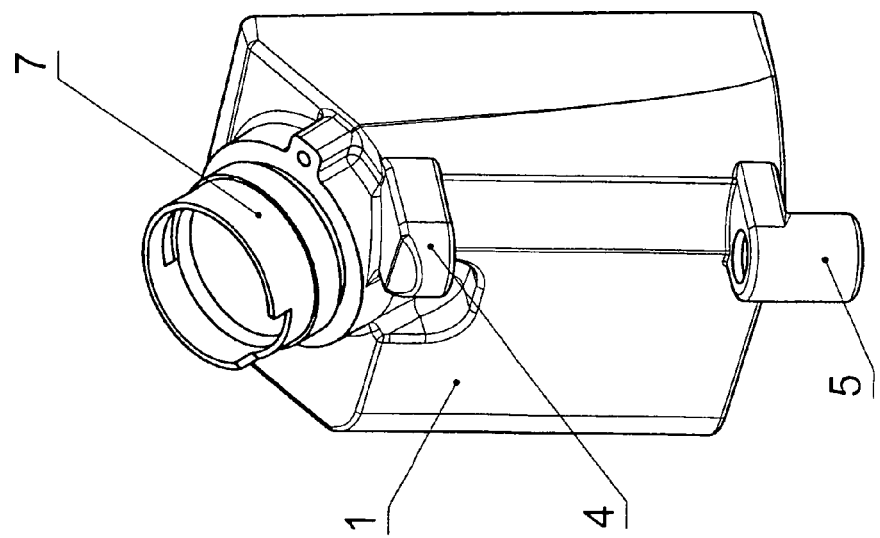
Fig. 4
Fig. 3
Fig. 2

US 7,648,039 B2

PRESSURE-RESISTANT TANK FOR LIQUIDS

CROSS REFERENCE TO RELATED APPLICATIONS

This application claims the benefit of priority under 35 U.S.C. § 119 of German Application DE 10 2004 041 448.3 filed Aug. 27, 2004, the entire contents of which are incorporated herein by reference.

FIELD OF THE INVENTION

The present invention pertains to a pressure-resistant tank for liquids, particularly for liquids which readily evaporate under ambient conditions.

BACKGROUND OF THE INVENTION

Such tanks for liquids contain, in general, a refillable reserve of a liquid which readily evaporates under ambient conditions and will be released for further consumption, especially in a downstream dispensing means. The liquid may be, for example, a propellant, a liquid means of production or even an anesthetic that readily evaporates under ambient conditions, for example, desflurane. It is necessary in the latter case that a tank suitable for such liquids be resistant for an internal pressure of, e.g., up to $4 \cdot 10^5$ Pascal and be designed for safety reasons for pressures of up to, e.g., $8 \cdot 10^5$ Pascal.

A prior-art anesthetic tank is described in DE 35 23 948 C2. Deep-drawn special steel plates were hitherto used for the wall material, which were soldered together manually. The sensor and functional elements and the heating element necessary for the controlled release of desflurane vapor was hitherto connected only by means of additionally soldered components. All connection geometries are arranged for this purpose by means of individually soldered special steel inserts. To guarantee the necessary pressure resistance, the deep-drawn plates must be connected with one another by a plurality of soldered webs. A gas line system, which makes possible the direct connection of a level indicator or valves, has so far not been embodied within such tanks for liquids in the known technical solutions.

SUMMARY OF THE INVENTION

It is an object of the present invention to provide a pressure-resistant tank for liquids that makes it possible to connect various functional and sensor elements directly and in such a way that space is saved.

It is a further and object of the present invention to provide a pressure-resistant tank for liquids that is simple in design, rugged in construction and economical to manufacture.

The use of diecast parts made of cast aluminum alloy makes possible the direct and space-saving connection and introduction of sensor and functional elements, such as a level indicator, temperature sensor system, refilling device, gas-carrying hole system for releasing the vapor, valve seats as well as a heating element thanks to the casting of different geometries. The integration of this plurality of functions directly in the tank for liquids has not hitherto been possible. Plastics with suitable strength and chemical resistance are several times more expensive. In addition, good thermal conductivity is necessary for the heating by a heating cartridge in case of an anesthetic tank, because very rapid heating is required when anesthetic is being refilled in order to ensure readiness to operate for the controlled release of anesthetic vapor.

Moreover, the heat must be introduced everywhere to prevent vapor from condensing especially in the gas-carrying holes of an anesthetic tank and to prevent errors in metering as a result of drop formation. Furthermore, the joining of two plastic parts with the requirements imposed in terms of tightness and pressure resistance is likewise problematic.

The geometry of the tank, which can be selected extensively freely due to the casting method, makes possible the excellent adaptation of the tank to the free spaces available at the time of the integration in an overall device and thus the optimal utilization of the space available for the installation with maximum filling volume. In addition, the use of aluminum instead of special steel has the advantage that the weight is reduced and the base material can be finished by machining in a simple manner. Due to the gas-tight connection of the diecast parts with the use of a second aluminum alloy by means of a closed weld seam welded with an electron beam, it is possible to manufacture the pressure-resistant tank for liquids.

The second aluminum alloy may advantageously have a hydrogen content of less than 0.2 mL per 100 g of wrought alloy.

The tank for liquids with the above noted features was particularly advantageous as an anesthetic tank of an anesthetic dispensing unit. The tank was particularly advantageous where the liquid is desflurane.

The second aluminum alloy, namely, the wrought alloy, for connecting the diecast parts may advantageously be is in the form of a welded frame. This welded frame can then connect a first, front diecast part with a second, rear diecast part.

The tank for liquids according to the invention may advantageously have an oxide layer, which is preferably applied by means of the anodization process.

Particularly with the tank of the invention provided as an anesthetic tank of an anesthetic dispensing unit, the rear diecast part may advantageously have a receiving channel for receiving an electric heating cartridge.

An exemplary embodiment of the present invention will be explained below on the basis of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 2 is a three-dimensional view of the first, front diecast part of the tank for liquids of FIG. 1;

FIG. 3 is a three-dimensional view of the welded frame arranged between the front and rear diecast parts of FIG. 1;

FIG. 4 is a three-dimensional view of the second, rear diecast part of the tank for liquids of FIG. 1.

DESCRIPTION OF THE PREFERRED EMBODIMENTS

Figure 1:
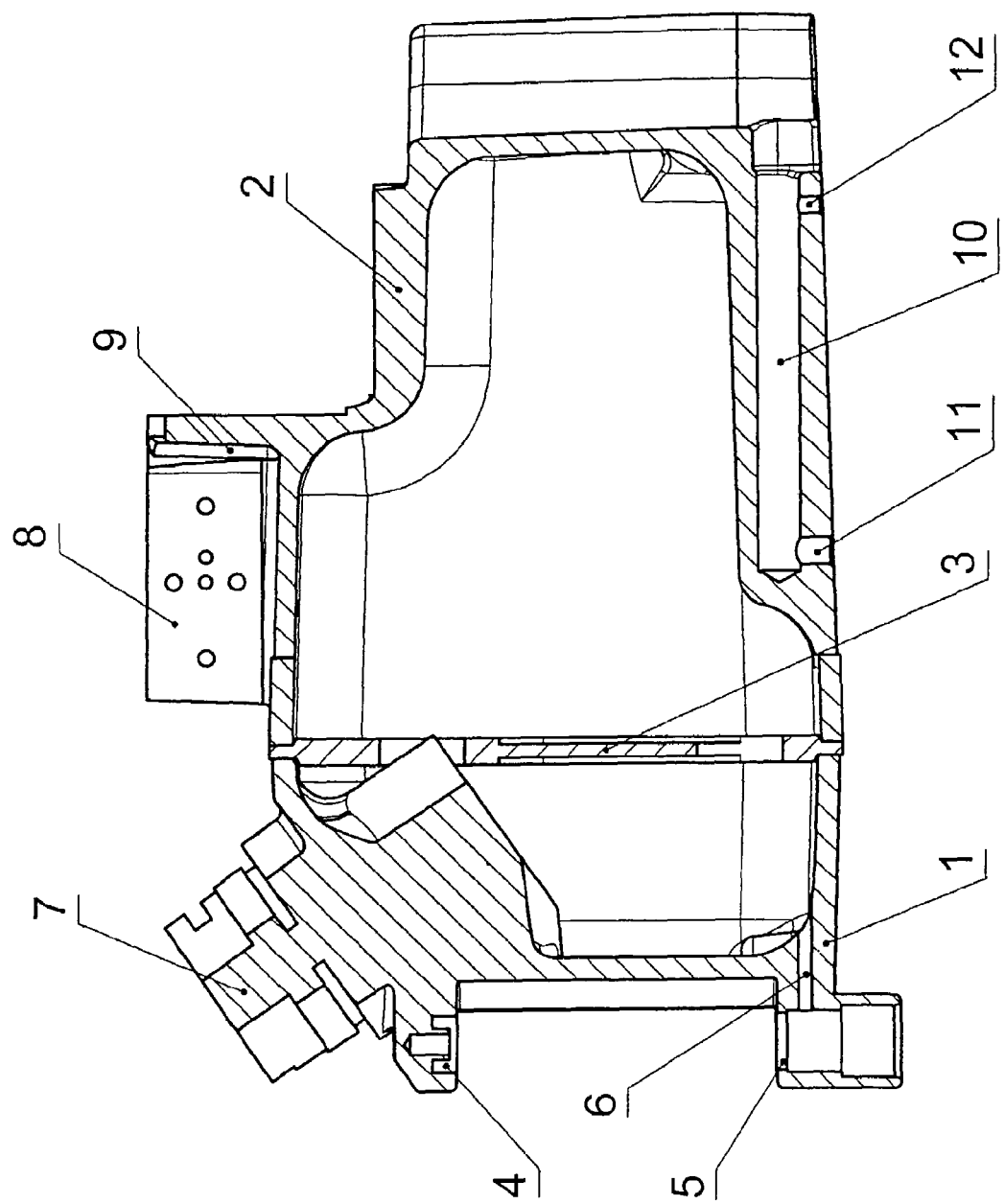
FIG. 1 is a vertical sectional view taken in the longitudinal direction of a tank for liquids according to the invention.

Referring to the drawings in particular, a pressure-resistant tank for liquids according to the invention is shown in FIG. 1. This is an anesthetic tank, which is used, for example, for the anesthetic desflurane combined with a downstream anesthetic dispensing unit, not shown. Desflurane is relatively volatile under ambient conditions and is released in a controlled manner in the form of a vapor from the heated anesthetic tank to the downstream dispensing means for the desired anesthesia of a patient.

The anesthetic tank being shown comprises two diecast parts 1, 2 made of a first cast aluminum alloy with the numerical alloy name EN AC-43400 and with the chemical symbols AlSi10Mg(Fe).

The front diecast part 1 has, in particular, upper and lower mounting elements 4, 5 for mounting a level tube, not shown, with a connection hole 6 for the equalization of the liquid with the interior space of the anesthetic tank. A connection part 7 is additionally provided for mounting a refilling cylinder containing anesthetic as well as with filling valve means, not shown, so that the refilling process begins only after the refilling cylinder has been screwed on reliably.

The rear diecast part 2 has, among other things, a receiving channel 10 for an electric heating cartridge, because the anesthetic desflurane is heated to an operating temperature above 40° C. The front hole 11 is used to receive a temperature sensor, and the rear hole 12 is to receive an adjusting element for the heating cartridge.

Furthermore, the rear diecast part 2 has gas-carrying discharge holes 9 for the release of anesthetic vapor as well as a mounting part 8 for dispensing valves, not shown, namely, a one-way valve and an associated proportional valve. The two diecast parts 1, 2 forming the housing tank are connected with one another in substance by an automatically prepared, closed weld seam. Diecast aluminum parts were hitherto believed not to be able to be welded in a gas-tight manner because the hydrogen inclusions present in them led to bursting of the weld seam, which made this porous and leaky. The use of diecast aluminum parts made of the alloy specified and the use of a second aluminum alloy for preparing the weld seam decisively improves weldability. The second aluminum alloy is a wrought aluminum alloy and consists of AlSi1MgMn and has a hydrogen content of less than 0.2 mL per 100 g of alloy. In particular, a welded frame 3 with passage openings for anesthetic (FIG. 3), which is made of this wrought alloy, is used. The welded frame 3 increases the strength of the anesthetic tank welded together and is used at the same time to improve the welding process. The joining of the components by an electron beam welding process under vacuum conditions makes it possible to prepare a nearly gas-tight weld seam free from pinholes. The part to be welded is turned automatically in an evacuated chamber in a device and bombarded with an electron beam. The accurately controllable welding depth makes it possible to weld into the welded frame 3 through the wall of the tank. A gap is prevented as a result from forming, so that crevice corrosion is made impossible by design. The vacuum supports the release of gases from the weld seam and thus the subsequent tightness of the tank.

To attain an oxidation resistance of the anesthetic tank that is sufficient for anesthetics, the tank is coated inside and outside according to an anodization method, the "hard anodization" being selected here. The method is based on electrolysis, i.e., the aluminum parts are electrolytically oxidized. The aluminum material is suspended in a dilute acid bath and connected as a positive electrode. For example, titanium is used as the negative electrode. If an electric voltage is applied to the electrodes, hydrogen gas develops at the cathode, and oxygen gas at the anode or the material. The oxygen reacts with the aluminum to form aluminum oxide, which forms an oxide film on the surface. The hard anodization takes place at 0° C. in order to inhibit the redissolution of the aluminum oxide. Greater layer thicknesses are obtained with higher voltages.

While a specific embodiment of the invention has been shown and described in detail to illustrate the application of the principles of the invention, it will be understood that the invention may be embodied otherwise without departing from such principles.

What is claimed is:

1. A pressure-resistant tank for liquids, comprising:
    a plurality of shaped diecast parts made of a first cast aluminum alloy;
    a second aluminum alloy comprising a wrought alloy;
    a closed weld seam connecting each of said diecast parts with said second aluminum wrought alloy such that said diecast parts connected with said second aluminum wrought alloy via said closed weld seam form a sealed anesthetic tank structure for receiving an anesthetic liquid, said diecast parts with said second aluminum wrought alloy being welded to form said closed weld seam with an electron beam.

2. A pressure-resistant tank for liquids in accordance with claim 1, wherein said second aluminum alloy has a hydrogen content of less than 0.2 mL per 100 g of wrought alloy.

3. A pressure-resistant tank for liquids in accordance with claim 1, wherein said anesthetic tank structure contains anesthetic for an anesthetic dispensing unit.

4. A pressure-resistant tank for liquids in accordance with claim 1, wherein said anesthetic liquid is desflurane.

5. A pressure-resistant tank for liquids in accordance with claim 1, wherein said second aluminum alloy connecting said diecast parts is a wrought alloy in the form of a welded frame.

6. A pressure-resistant tank for liquids in accordance with claim 5, wherein said plurality of shaped diecast parts comprise a first front diecast part and a second rear diecast part and said welded frame connects said first front diecast part with said second rear diecast part.

7. A pressure-resistant tank for liquids in accordance with claim 1, further comprising an oxide layer applied by means of an anodization process.

8. A pressure-resistant tank for liquids in accordance with claim 6, wherein said rear diecast part has a receiving channel for receiving an electric heating cartridge.

9. A pressure-resistant tank for liquids in accordance with claim 1, further comprising an oxide layer applied on an exterior of said plurality of shaped diecast parts, said second aluminum alloy and said closed weld seam.

10. A pressure-resistant tank for liquids, formed by the steps comprising:
    forming a first front diecast part and a second rear diecast part of a first aluminum cast alloy, said first front diecast part having a first diecast part edge surface, said second rear diecast part having a second diecast part edge surface;
    forming a frame of a second aluminum alloy comprising a wrought alloy, said frame having a front frame edge surface and a rear frame edge surface;
    welding the first front diecast part edge surface of said first front diecast part to the front frame edge surface of the second aluminum alloy frame with a closed weld seam using an electron beam;
    welding the second diecast part edge surface of the second rear diecast part to said rear frame edge surface of the second aluminum alloy frame with another closed weld seam using an electron beam such that said frame of said second aluminum alloy is located between said first front diecast part edge surface of said first front diecast part and said second diecast part edge surface of said second rear diecast part.

11. A pressure-resistant tank for liquids in accordance with claim 10, wherein said second aluminum alloy is provided having a hydrogen content of less than 0.2 mL per 100 g of wrought alloy.

12. A pressure-resistant tank for liquids in accordance with claim 1, further comprising using an anodization process to apply an oxide layer to the welded diecast parts.

13. A pressure-resistant tank for liquids in accordance with claim 6, wherein said rear diecast part is formed with a receiving channel for receiving an electric heating cartridge.

14. A pressure-resistant tank for liquids in accordance with claim 10, wherein said front frame edge surface having a front frame edge surface contour, said rear frame edge surface having a rear frame edge surface contour, said first diecast part edge surface having a first edge surface contour, said first edge surface contour being substantially similar to said front frame edge surface contour, said second diecast part edge surface having a second edge surface contour, said second edge surface contour being substantially similar to said rear frame edge surface contour, wherein said first front diecast part, said second rear diecast part and said frame form a sealed anesthetic tank structure for receiving an anesthetic liquid.

15. A pressure-resistant tank for liquids in accordance with claim 10, wherein said first front diecast part has mounting elements for mounting a level tube and a connection part for mounting a refilling cylinder.

16. A pressure-resistant tank for liquids in accordance with claim 15, wherein said second rear diecast part has a receiving channel for receiving an electric heating cartridge and gas-carrying discharge holes for releasing vapor, said second rear diecast part having a mounting part for attaching dispensing valves thereto, said second rear diecast part defining a front hole for receiving a temperature sensor and a rear hole for receiving an adjusting element of the heating cartridge.

17. A pressure-resistant tank for liquids in accordance with claim 16, wherein said frame defines one or more openings, said openings being in communication with an interior of said first front die part and with an interior of said second rear diecast part.

18. A pressure-resistant tank for liquids in accordance with claim 5, wherein said plurality of shaped diecast parts comprise a first front diecast part and a second rear diecast part, said first front diecast part having a first diecast part edge surface, said second rear diecast part having a second diecast part edge surface, said frame having a front frame edge surface and a rear frame edge surface, said first front diecast part edge surface of said first front diecast part being welded to the front frame edge surface of said frame with one said closed weld seam, said second diecast part edge surface of the second rear diecast part being welded to said rear frame edge surface of the second aluminum alloy frame with another said closed weld seam such that said frame is located between said first front diecast part edge surface of said first front diecast part and said second diecast part edge surface of said second rear diecast part.

19. A pressure-resistant tank for liquids in accordance with claim 18, said front frame edge surface having a front frame edge surface contour, said rear frame edge surface having a rear frame edge surface contour, said first diecast part edge surface having a first edge surface contour, said first edge surface contour being substantially similar to said front frame edge surface contour, said second diecast part edge surface having a second edge surface contour, said second edge surface contour being substantially similar to said rear frame edge surface contour.

20. A pressure-resistant tank for liquids in accordance with claim 19, wherein said first front diecast part has mounting elements for mounting a level tube and a connection part for mounting a refilling cylinder, said second rear diecast part having a receiving channel for receiving an electric heating cartridge and gas-carrying discharge holes for releasing vapor, said second rear diecast part having a mounting part for attaching dispensing valves thereto, said second rear diecast part defining a front hole for receiving a temperature sensor and a rear hole for receiving an adjusting element of the heating cartridge, said frame defining one or more openings, said openings being in communication with an interior of said first front die part and with an interior of said second rear diecast part.

* * * * *